(12) United States Patent
   Zachek

(10) Patent No.: US 12,611,502 B2
(45) Date of Patent: Apr. 28, 2026

(54) MODULAR POWER AND CONNECTIVITY SYSTEM FOR INFUSION DEVICES

(71) Applicant: CAREFUSION 303, INC., San Diego, CA (US)

(72) Inventor: Matthew Kendrick Zachek, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 142 days.

(21) Appl. No.: 17/123,899

(22) Filed: Dec. 16, 2020

(65) Prior Publication Data

US 2021/0178055 A1    Jun. 17, 2021

Related U.S. Application Data

(60) Provisional application No. 62/949,305, filed on Dec. 17, 2019.

(51) Int. Cl.
   *A61M 5/14*       (2006.01)
   *G16H 20/17*     (2018.01)
   *G16H 40/67*     (2018.01)

(52) U.S. Cl.
   CPC .......... *A61M 5/1413* (2013.01); *G16H 20/17* (2018.01); *G16H 40/67* (2018.01);
   (Continued)

(58) Field of Classification Search
   CPC ........ A61M 5/1413; A61M 2205/3553; A61M 2205/8206; A61M 2205/8237;
   (Continued)

(56) References Cited

U.S. PATENT DOCUMENTS 7,163,381 B1    1/2007  Barak
7,713,240 B2 *  5/2010  Istoc .................. A61B 5/14532
                                                            604/151
(Continued)

FOREIGN PATENT DOCUMENTS

CN           1556716 A     12/2004
CN        102939121 A      2/2013
(Continued)

OTHER PUBLICATIONS

International Search Report and Written Opinion for Application No. PCT/US2020/065399, dated Mar. 30, 2021, 16 pages.
(Continued)

*Primary Examiner* — Bhisma Mehta
*Assistant Examiner* — Fatimata Sahra Diop
(74) *Attorney, Agent, or Firm* — MASCHOFF BRENNAN

(57)           ABSTRACT

A modular power and connectivity assembly and system are provided. The modular power and connectivity assembly includes a housing, a power assembly and a communication assembly. The modular power and connectivity assembly is reusable and provides power and communications to a removably coupled infusion device. The system includes multiple modular power and connectivity assemblies, a charging station for recharging the modular power and connectivity assemblies, a connectivity hub for communicating with the modular power and connectivity assemblies, and a cloud interface to a healthcare system for sending and receiving information to and from the modular power and connectivity assemblies. A method of operating a modular power and connectivity system is also provided.

17 Claims, 6 Drawing Sheets

(52) U.S. Cl.
CPC .............. *A61M 2205/3553* (2013.01); *A61M 2205/8206* (2013.01); *A61M 2205/8237* (2013.01)

(58) Field of Classification Search
CPC ...... A61M 2205/12; A61M 2205/3334; A61M 2205/3561; A61M 2205/3569; A61M 2205/3584; A61M 2205/3592; A61M 2205/50; A61M 2209/086; A61M 5/142; A61M 5/16854; A61M 5/486; G16H 20/17; G16H 40/67
See application file for complete search history.

(56)           References Cited

U.S. PATENT DOCUMENTS

|  |  |  |  |  |
|---|---|---|---|---|
| 8,752,436 | B2 * | 6/2014 | Beck .................... | G01L 9/0027 |
|  |  |  |  | 73/756 |
| 11,302,432 | B2 * | 4/2022 | Tsoukalis ............... | G16H 20/17 |
| 2007/0060871 | A1 | 3/2007 | Istoc et al. | |
| 2011/0306859 | A1 | 12/2011 | Saldivar et al. | |
| 2012/0053520 | A1 | 3/2012 | Kirkpatrick | |
| 2012/0068919 | A1 * | 3/2012 | Lauder .................. | G06F 1/1677 |
|  |  |  |  | 345/156 |
| 2012/0078218 | A1 | 3/2012 | Barnes | |
| 2014/0275725 | A1 | 9/2014 | Schenck et al. | |
| 2014/0336576 | A1 | 11/2014 | Gamelin | |
| 2016/0038675 | A1 * | 2/2016 | Estes ................... | A61M 5/1723 |
|  |  |  |  | 604/151 |
| 2016/0051750 | A1 | 2/2016 | Tsoukalis | |
| 2018/0028745 | A1 | 2/2018 | Amon et al. | |
| 2018/0099090 | A1 * | 4/2018 | Miyamoto ........ | A61M 5/16831 |
| 2018/0214636 | A1 * | 8/2018 | Amirouche ....... | A61M 5/14248 |
| 2022/0001105 | A1 * | 1/2022 | Shmilovich ....... | A61M 5/16827 |

FOREIGN PATENT DOCUMENTS

| CN | 203954341 | U | 11/2014 |
|---|---|---|---|
| CN | 105188796 | A | 12/2015 |
| CN | 108697845 | A | 10/2018 |
| CN | 108744139 | A | 11/2018 |
| CN | 110013577 | A | 7/2019 |
| JP | H01073224 | A | 3/1989 |
| JP | 2009507607 | A | 2/2009 |
| JP | 2016515000 | A | 5/2016 |
| WO | WO-2012040249 | A2 | 3/2012 |

OTHER PUBLICATIONS

Chinese Office Action for Application No. 202080087882.3, dated Aug. 30, 2024, 14 pages including translation.

Japanese Office Action for Application No. 2022-535134, dated Oct. 1, 2024, 7 pages including translation.

Chinese Office Action for Application No. 202080087882.3, dated Jan. 3, 2024, 19 pages including translation.

Chinese Notification to Grant for Application No. 202080087882.3, dated Jan. 21, 2025, 6 pages including translation.

Chinese Office Action for Application No. 202080087882.3, dated Nov. 11, 2024, 21 pages including translation.

European Office Action for Application No. 20842406.9, dated Dec. 23, 2024, 5 pages.

Japanese Decision of Rejection for Application No. 2022-535134, dated Feb. 21, 2025, 5 pages including translation.

Australian Office Action for Application No. 2020404994, dated Jul. 25, 2025, 4 pages.

Australian Office Action for Application No. 2020404994, dated Feb. 13, 2026, 4 pages.

* cited by examiner

High-Level System Architecture

MODULAR POWER AND CONNECTIVITY SYSTEM FOR INFUSION DEVICES

CROSS-REFERENCES TO RELATED APPLICATIONS

This application claims the benefit of U.S. Provisional Patent Application No. 62/949,305 entitled "MODULAR POWER AND CONNECTIVITY SYSTEM FOR INFUSION DEVICES," filed on Dec. 17, 2019, the disclosure of which is hereby incorporated by reference in its entirety for all purposes.

TECHNICAL FIELD

The present disclosure generally relates to power and connectivity for devices, and in particular a modular system for power and connectivity of infusion devices.

BACKGROUND

Infusion devices are used in the medical field for intravenous (IV) applications. Typical infusion devices require independent power and connectivity to provide the desired infusion outcome. Typical infusion systems require a physical connection of each infusion device to existing infrastructure and/or require each device to include its own power source and connectivity hardware, thus causing increased costs and/or creating undesirable tradeoffs in infusion workflow. For example, typical infusion devices follow an "all in one" approach in which all aspects (e.g., power, connectivity) of the infusion device are contained within the device. However, infusion set devices (e.g., IV line components) are generally disposable single-use devices, making the disposal of high cost components undesirable.

Thus, it is desirable to provide a non-disposable modular power and connectivity assembly for disposable infusion devices.

SUMMARY

One or more embodiments provide a modular power and connectivity assembly. The modular power and connectivity assembly includes a housing comprising a cavity configured to receive a device coupling member, a power assembly configured to provide power to the infusion device, and a communication assembly configured to provide communication with the infusion device. The modular power and connectivity assembly is configured to be reusable and to be removably coupled to the infusion device One or more embodiments provide a power and connectivity system. The power and connectivity system includes one or more reusable modular power and connectivity assemblies. Each reusable modular power and connectivity assembly includes a housing having a cavity configured to receive a device coupling member, a power assembly configured to provide power to the infusion device, and a communication assembly configured to provide communication with the infusion device. Each modular power and connectivity assembly is configured to be removably coupled to an infusion device. The power and connectivity system also includes a connectivity hub configured to transmit electronic signals to and receive electronic signals from the one or more reusable modular power and connectivity assemblies.

One or more embodiments provide a method of operating a modular power and connectivity system. The method includes removably coupling the modular power and connectivity assembly to an infusion device; transmitting power from the modular power and connectivity assembly to the infusion device; providing a communication link between the modular power and connectivity assembly and the infusion device; transmitting data from the infusion device to the modular power and connectivity assembly; transmitting at least a portion of the data from the modular power and connectivity assembly to a connectivity hub; and transmitting the portion of the data from the connectivity hub to a cloud interface of a healthcare network.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The subject technology provides a modular approach with independent power and connectivity. For example, a non-disposable, rechargeable power supply that enables functionality of a disposable peripheral infusion device (e.g., sensors, pumping elements). The modular design provides for a lower total device cost, a lower environmental impact from disposal of electronics, prevents misconnections of devices, and prevents cyber security risks via a proprietary interface. The modular approach further lowers the cost burden for consumers by separating high-cost non-disposable componentry (e.g., battery, communications interface) from low-cost disposable componentry (e.g., sensor, pumping element).

Figure 1:
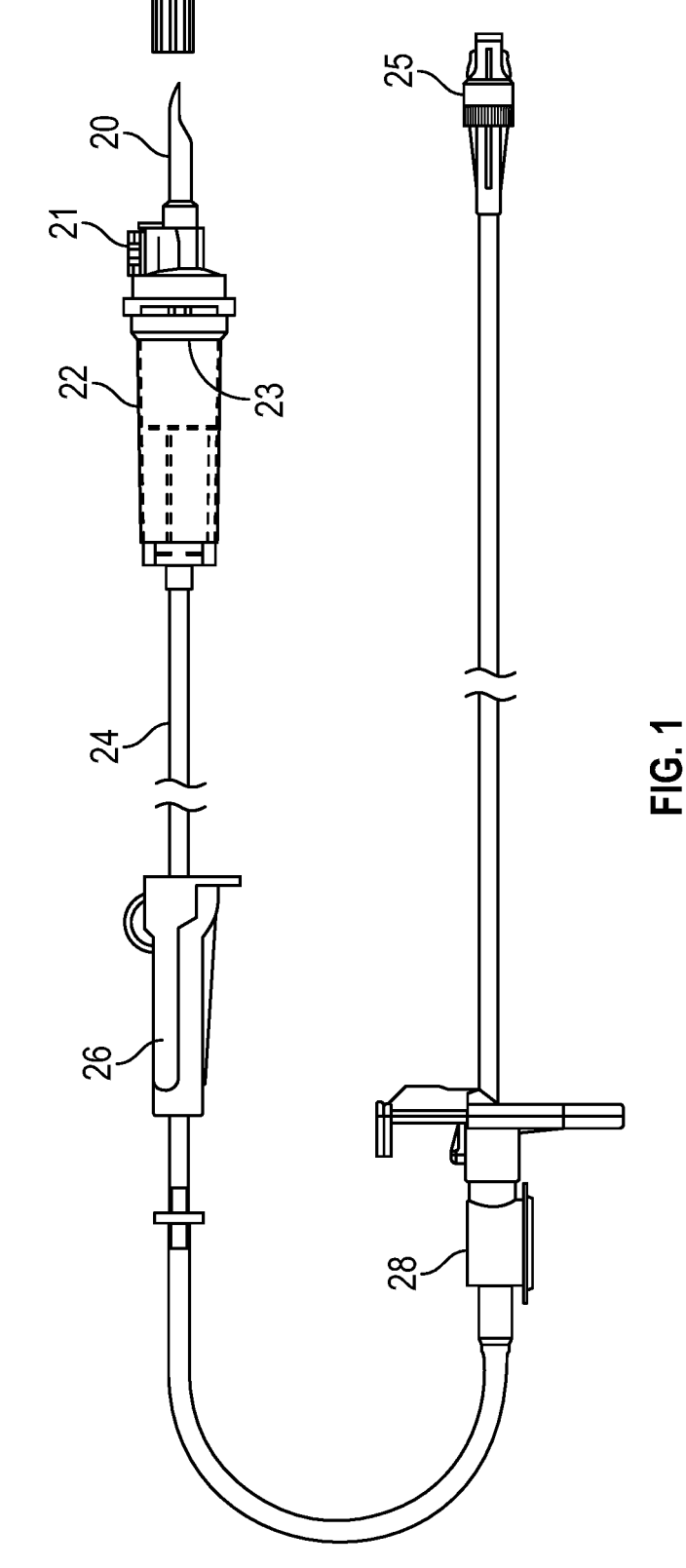
FIG. 1 depicts a schematic view of an example infusion set with a typical infusion device.

The present disclosure relates to an infusion device assembly such as a non-disposable modular power and connectivity assembly for infusion devices. The modular power and connectivity assembly may provide power and connectivity to any desired infusion device (e.g., sensor, pump). Typically, a standard infusion set 10 is used to infuse fluid to a subject. An example of a standard infusion set 10 is shown in FIG. 1.

The infusion set 10 includes a piercing spike 20 which may either be a sharp spike for piercing rubber stoppers or rounded and blunt for insertion into a bag (not shown). The spike 20 contains one channel for fluid and optionally a second channel for venting. A vent 21 is usually present in the vicinity of the piercing spike 20 to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with liquid. This prevents air bubbles from entering the connector tube 24, which would be harmful to a patient. A particle filter (not shown) may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube 24.

At the end of the connector tube 24 is a Luer fitting 25 which is standardized for connection to all other pieces of apparatus having a standard Luer cone. The person skilled in the art will appreciate that the Luer fitting 25 can be fitted to an infusion pump or a hypodermic needle (not shown) for infusing the medical fluid into the circulatory system of a patient (e.g., into a vein).

Between the drop chamber 22 and the Luer fitting 25 and engaging with the connector tube 24, is a roller clamp 26 for controlling a flow rate of fluid through the connector tube 24. Also between the drop chamber 22 and the Luer fitting 25 and engaging with the connector tube 24, is an infusion device 28 (e.g., pressure sensor). The infusion device 28 typically requires a connection to a hardwired power source, such as a power cable/wire connection between the infusion device 28 and an electrical outlet, for example. Communications to/from the infusion device 28 typically requires a connection to a hardware communication device, such as a communication cable/wire connection between the infusion device 28 and a router, for example.

Figure 2:
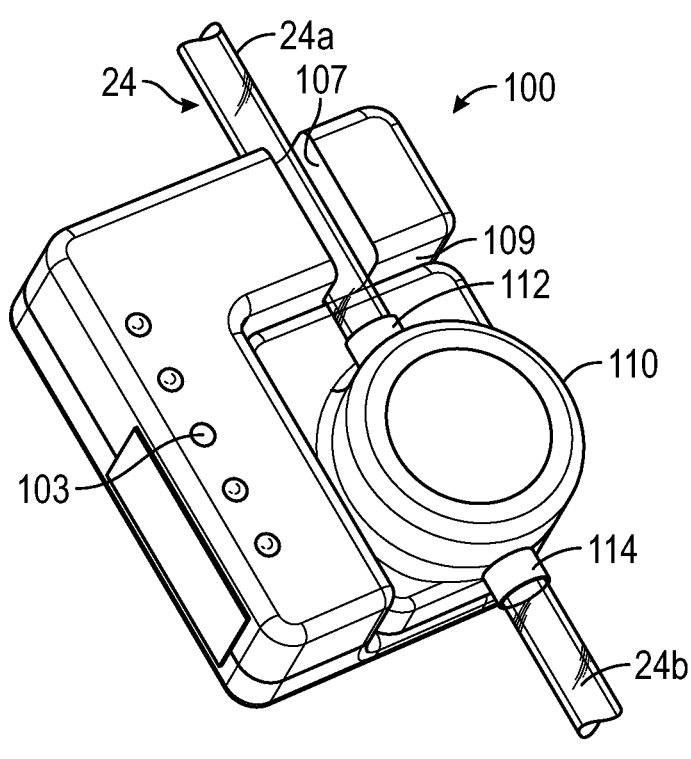
FIG. 2 depicts a perspective view of a modular power and connectivity assembly, according to aspects of the subject technology.

With reference to FIG. 2, a modular power and connectivity assembly 100 for infusion devices is shown. The modular power and connectivity assembly 100 has a housing 105 dimensioned and configured to receive an infusion device 110 (e.g., sensor device, pump device). For example, the infusion device 110 may be a sensor for sensing pressure of a fluid flowing through the tube 24. The housing 105 may also be dimensioned and configured to receive tubing, such as connector tube 24. For example, housing 105 may include a tube recess 107 sized and configured to receive the tube 24, which may assist in keeping the tube 24 coupled to the infusion device 110, help prevent kinking or displacement of the tube 24, and/or assist in coupling the infusion device 110 to the modular power and connectivity assembly 100.

The modular power and connectivity assembly 100 may be configured as a non-disposable device that may be repeatedly used to provide power and/or communications for multiple disposable infusion sets 10 and/or disposable infusion devices 110. For example, the modular power and connectivity assembly 100 may be used to provide power and communications to a first disposable infusion device 110, after which the first disposable infusion device 110 is thrown away and modular power and connectivity assembly 100 may be used to provide power and communications to a second disposable infusion device 110. The second disposable infusion device 110 may be used with the same infusion set that the first disposable infusion device 110 was used with, such as replacing a first pressure sensor with a second pressure sensor if the first pressure sensor goes bad or if a different type of pressure sensor is needed during an infusion process using the infusion set. In another example, the second disposable infusion device 110 may be used with a different infusion set, such as with the same patient in a different infusion process or with a new patient.

In use, an infusion device 110 may be on or attached to an infusion line, such as tube 24. For example, FIG. 2 shows an infusion device 110 with a fluid inlet 112 coupled to a first tube 24a and a fluid outlet 114 coupled to a second tube 24b. Here, fluid may flow in from the first tube 24a, through the infusion device 110 (e.g., pressure sensor, pump element) and out through the second tube 24b, so that the infusion device 110 may observe or monitor aspects of the fluid (e.g., fluid pressure, fluid color, presence of gas bubbles) as the fluid passes through, and/or act upon the fluid (e.g., pump the fluid, filter the fluid, mix a gas/other fluid into the fluid).

As shown in FIG. 2, the modular power and connectivity assembly 100 is removably coupled to the infusion device 110. The housing 105 may include a receiving cavity or cutout 109 that is sized and dimensioned to receive the infusion device 110. The housing 105 and the infusion device 110 may be coupled in any desired manner. For example, the housing 105 and the infusion device 110 may have magnetic elements that are attracted to each other. In another example, the receiving cavity 109 may include one or more engagement members (e.g., snap, socket, pin, Velcro, tab) configured to engage with opposing engagement members on the infusion device 110. Thus, the modular power and connectivity assembly 100 may be easily connected to or disconnected from the infusion device 110, either prior to or after the infusion device 110 and the tube 24 are connected.

The coupling between the housing 105 and the infusion device 110 may include a power connection (e.g., pin, cable) configured to provide power from the modular power and connectivity assembly 100 to the infusion device 110 upon physical coupling of the connectivity assembly 100 to the infusion device 110. The power connection may be configured as a wireless power transmission, where the housing 105 may have a wireless power transmitter and the infusion device 110 may have a wireless power receiver. Accordingly, the infusion device 110 may not require a physical connection to the modular power and connectivity assembly 100 as power may be transmitted to the infusion device 110 when the infusion device 110 is within proximity to the modular power and connectivity assembly 100.

Similarly, the coupling between the housing 105 and the infusion device 110 may include a communication connection (e.g., pin, cable) configured to provide communications between the modular power and connectivity assembly 100 and the infusion device 110 upon physical coupling of the modular power and connectivity assembly 100 to the infusion device 110. The communication connection may be configured as a wireless communication transmission (e.g., Bluetooth, WiFi, Zigbee) where the housing 105 and the infusion device 110 may each have a wireless communication component (e.g., transmitter, receiver, transceiver). Accordingly, the infusion device 110 may not require a physical connection to the modular power and connectivity assembly 100 as communications may be transmitted and received when the infusion device 110 is within proximity to the modular power and connectivity assembly 100.

Figure 3:
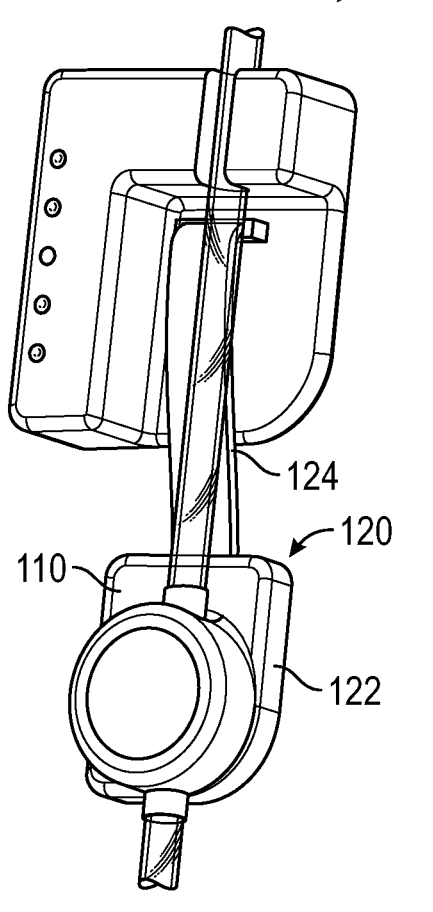
FIG. 3 depicts a perspective view of a modular power and connectivity assembly, according to aspects of the subject technology.

As shown in FIG. 3, the modular power and connectivity assembly 100 may include a harness assembly 120. The harness assembly 120 may include a base 122 and an extension member 124. Here, the infusion device 110 may be coupled to the base 122 (e.g., pins, magnets) and the extension member 124 may couple the base 122 to the housing 105. The extension member 124 may include power and/or communication wires to provide power and/or communications transmission between the modular power and connectivity assembly 100 and the base 122. The base 122 may be configured to provide power to and/or communications to/from the infusion device 110 as discussed above (e.g., physical or wireless transmission). In another example, the extension member 124 may not provide physical power/communication connections (e.g., formed of a non-conductive material) and power/communications may be transmitted wirelessly between the housing 105 and the base 122, and further transmitted between the base 122 and the infusion device 110. In yet another example, power/communications may be transmitted wirelessly directly between the housing 105 and the infusion device 110.

The modular power and connectivity assembly 100 may be configured to use the harness assembly 120 if the infusion device 110 is not sized to fit within the cavity 109, such as if the infusion device 110 is larger than the cavity 109 or the infusion device 110 requires connections to other tubes and/or devices. As another example, the modular power and connectivity assembly 100 may be configured to use the harness assembly 120 in most or all operations, such as even if the infusion device 110 is sized to fit within the cavity 109. The harness assembly 120 may be configured to removably connect to a modular power and connectivity assembly 100, so that modular power and connectivity assembly 100 may be used in any configuration discussed above. As another example, the harness assembly 120 may be integrally formed with the housing 105.

The housing 105 may also include indicators 103 (e.g., LED lights) configured to provide visual indications of power levels in the modular power and connectivity assembly 100. For example, the modular power and connectivity assembly 100 may include one or more rechargeable batteries (e.g., lithium ion) disposed within the housing 105. The indicators 103 may be configured to provide visual indication of the power left in the batteries. Indicators 103 may also be configured to provide visual indication of a communication link between the modular power and connectivity assembly 100 and the infusion device 110, for example.

Figure 4:
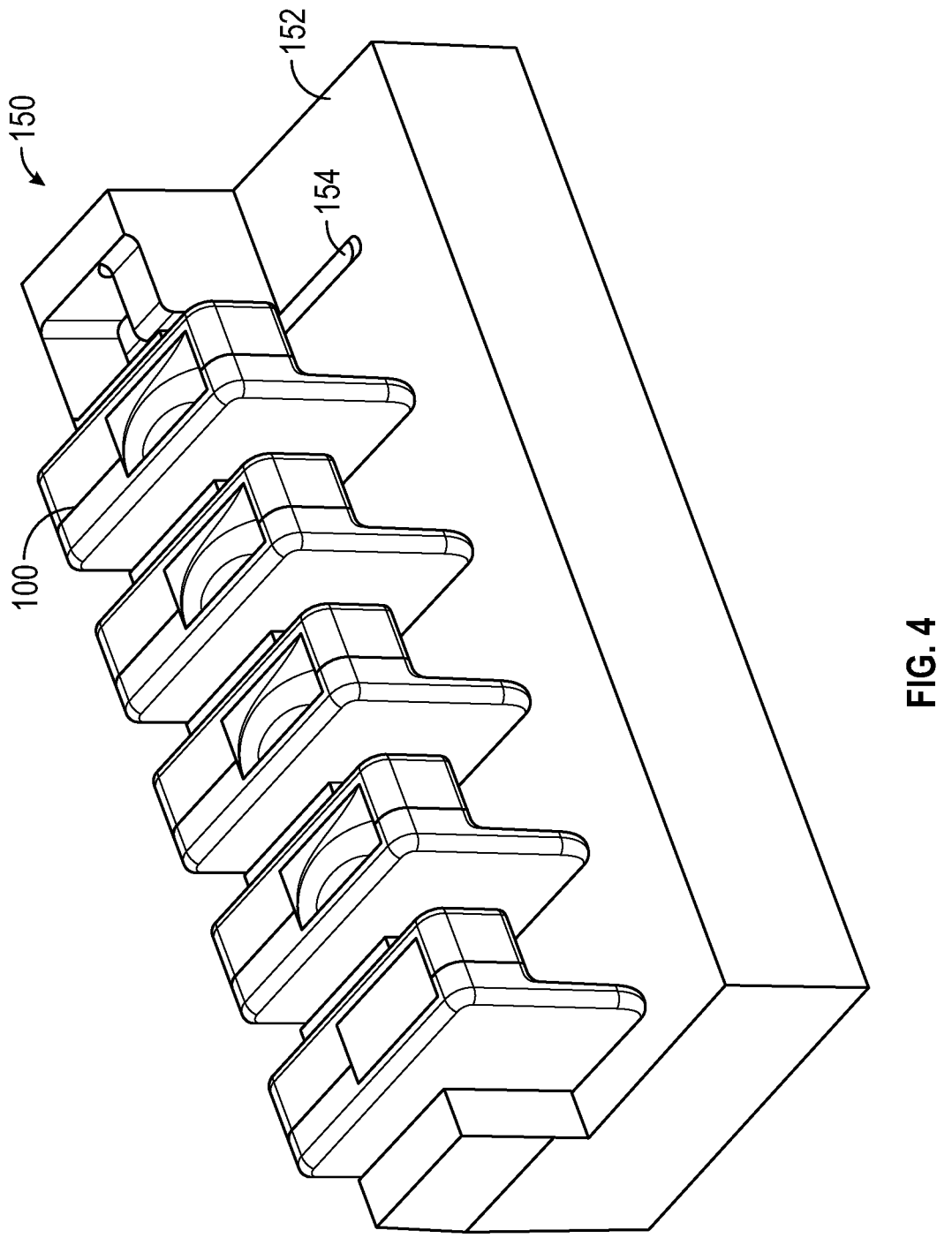
FIG. 4 depicts a perspective view of a charging station, according to aspects of the subject technology.

As depicted in FIG. 4, the subject technology may also include a charging station 150 configured to provide power for recharging one or more modular power and connectivity assemblies 100. For example, the charging station 150 may have a base 152 and receiving slots 154, where a modular power and connectivity assembly 100 may be inserted into a receiving slot 154. Power may be transmitted from the charging station 150 to the modular power and connectivity assembly 100 directly through a physical connection (e.g., pins, lands) between a portion of the modular power and connectivity assembly 100 and the base 152. Power may be transmitted from the charging station 150 to the modular power and connectivity assembly 100 indirectly via a wireless power connection.

The charging station 150 may be hardwired into a power source (e.g., building electrical wiring) such that the charging station 150 is generally permanently positioned in a particular location. The charging station 150 may be configured as a portable unit by including an electrical plug for plugging into an electrical outlet and/or a portable battery (e.g., rechargeable battery).

Figure 5:
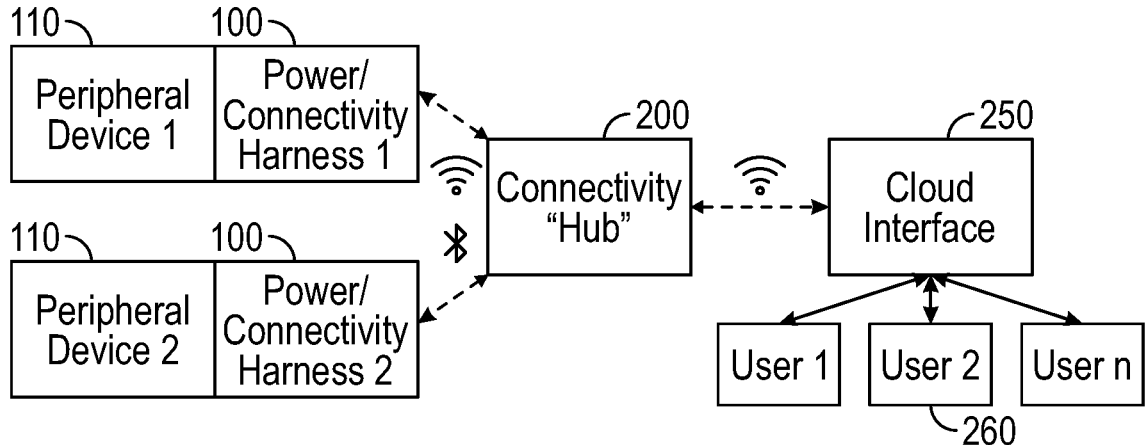
FIG. 5 depicts an example of a healthcare organization network, according to aspects of the subject technology.

As depicted in FIG. 5, the subject technology may also include a connectivity hub 200 configured to interconnect communications and/or control between modular power and connectivity assemblies 100 coupled to infusion devices 110 and a cloud interface 250 of an institutional patient care system of a healthcare organization having user devices 260. For example, the connectivity hub 200 may be configured to send/receive information between the modular power and connectivity assemblies 100 and the patient care system, providing for mobile control of the infusion devices 110 coupled to the modular power and connectivity assemblies 100.

Figure 6:
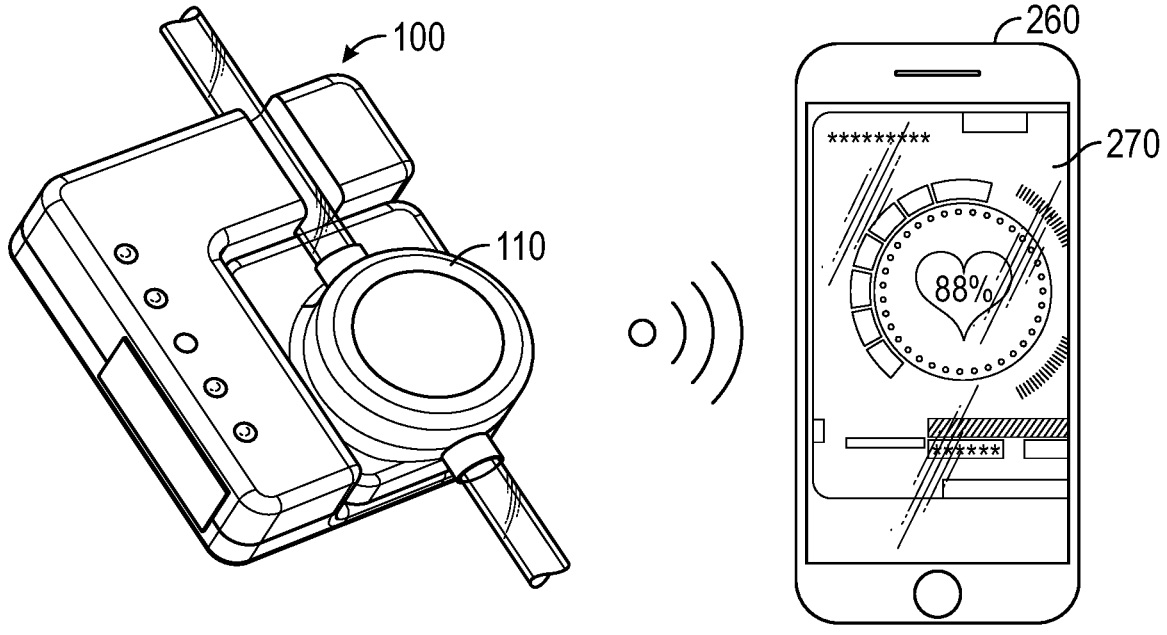
FIG. 6 depicts an example of a modular power and connectivity assembly in communication with a user device having an example graphical user interface, in accordance with aspects of the subject technology.

As shown in FIGS. 5 and 6, a modular power and connectivity assembly 100 may transmit information from the infusion device 110 (e.g., sensor information) through the connectivity hub 200 to the cloud interface 250 to a particular user device 260 (e.g., healthcare provider's smartphone). Thus, a healthcare provider may monitor an infusion process of a subject remotely. As another example, the information flow may be reversed, where the healthcare provider may enter an adjustment (e.g., change pump rate) on the user device 260, which is then transmitted from the cloud interface 250 to the connectivity hub 200 to the modular power and connectivity assembly 100 to an infusion device 110 (e.g., pump element). Thus, a healthcare provider may control an infusion process of a subject remotely. In one or more aspects of the subject technology, Bluetooth connectivity may be provided between the modular power and connectivity assemblies 100 and the connectivity hub 200, WiFi connectivity may be provided between the connectivity hub 200 and the cloud interface 250 and a mobile interface 270 may provide information connectivity between the cloud interface 250 and the user device 260.

Figure 7:
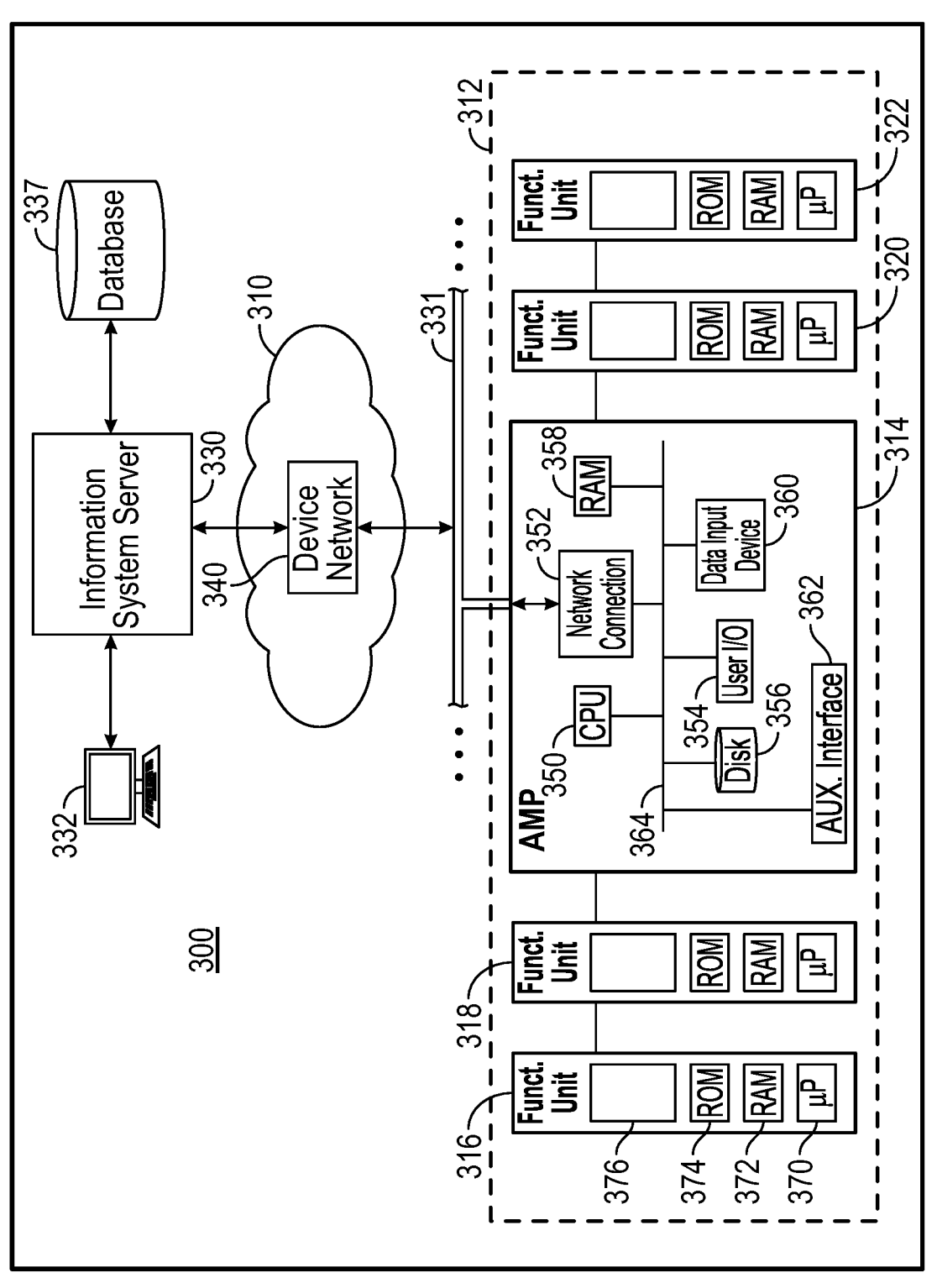
FIG. 7 depicts an example of an institutional patient care system of a healthcare organization, according to aspects of the subject technology.

FIG. 7 depicts an example of an institutional patient care system 300 of a healthcare organization, according to aspects of the subject technology. In FIG. 7, a patient care device (or "medical device" generally) 312 is connected to a healthcare facility network 310. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each medical device 312 is connected to an internal healthcare network 310 by a transmission channel 331. Transmission channel 331 is any wired or wireless transmission channel, for example an 802.11 wireless local area network (LAN). In some implementations, network 310 also includes computer systems located in various departments throughout a healthcare facility. For example, network 310 of FIG. 7 optionally includes computer systems associated with an admissions department, a billing department, a biomedical engineering department, a clinical laboratory, a central supply department, one or more unit station computers and/or a medical decision support system. As described further below, network 310 may include discrete subnetworks. In the depicted example, network 310 includes a device network 340 by which patient care devices 312 (and other devices) communicate in accordance with normal operations.

Additionally, institutional patient care system 300 may incorporate a separate information system server 330, the function of which will be described in more detail below. Moreover, although the information system server 330 is shown as a separate server, the functions and programming of the information system server 330 may be incorporated into another computer, if such is desired by engineers designing the institution's information system. Institutional patient care system 300 may further include one or multiple device terminals 332 for connecting and communicating with information system server 330. Device terminals 332 may include personal computers, personal data assistances, mobile devices such as laptops, tablet computers, augmented reality devices, or smartphones, configured with software for communications with information system server 330 via network 310.

Patient care device 312 comprises a system for providing patient care, such as that described in U.S. Pat. No. 5,713,856 to Eggers et al., which is incorporated herein by reference for that purpose. Patient care device 312 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 312 comprises a control module or unit 314, also referred to as interface unit 314, connected to one or more functional modules 316, 318, 320, 322. Interface unit 314 includes a central processing unit (CPU) 350 connected to a memory, for example, random access memory (RAM) 358, and one or more interface devices such as user interface device 354, a coded data input device 360, a network connection 352, and an auxiliary interface 362 for communicating with additional modules or devices. Interface unit 314 also, although not necessarily, includes a main non-volatile storage unit 356, such as a hard disk drive or non-volatile flash memory, for storing software and data and one or more internal buses 364 for interconnecting the aforementioned elements.

In various implementations, user interface device 354 is a touch screen for displaying information to a user and allowing a user to input information by touching defined areas of the screen. Additionally or in the alternative, user interface device 354 could include any means for displaying and inputting information, such as a monitor, a printer, a keyboard, softkeys, a mouse, a track ball and/or a light pen. Data input device 360 may be a bar code reader capable of scanning and interpreting data printed in bar coded format. Additionally or in the alternative, data input device 360 can be any device for entering coded data into a computer, such as a device(s) for reading a magnetic strips, radio-frequency identification (RFID) devices whereby digital data encoded in RFID tags or smart labels (defined below) are captured by the reader 360 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 354 and data input device 360 may be the same device.

Although data input device 360 is shown in FIG. 7 to be disposed within interface unit 314, it is recognized that data input device 360 may be integral within pharmacy system 334 or located externally and communicating with pharmacy system 334 through an RS-232 serial interface or any other appropriate communication means. Auxiliary interface 362 may be an RS-232 communications interface, however any other means for communicating with a peripheral device such as a printer, patient monitor, infusion pump or other medical device may be used without departing from the subject technology. Additionally, data input device 360 may be a separate functional module, such as modules 316, 318, 320 and 322, and configured to communicate with control unit 314, or any other system on the network, using suitable programming and communication protocols.

Network connection 352 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 316, 318, 320, 322 are any devices for providing care to a patient or for monitoring patient condition. As shown in FIG. 7, at least one of functional modules 316, 318, 320, 322 may be an infusion pump module such as an intravenous infusion pump for delivering medication or other fluid to a patient. For the purposes of this discussion, functional module 316 is an infusion pump module. Each of functional modules 318, 320, 322 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 318, 320 and/or 322 may be a printer, scanner, bar code reader or any other peripheral input, output or input/output device.

Each functional module 316, 318, 320, 322 communicates directly or indirectly with interface unit 314, with interface unit 314 providing overall monitoring and control of device 312. Functional modules 316, 318, 320, 322 may be connected physically and electronically in serial fashion to one or both ends of interface unit 314 as shown in FIG. 7, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 314. As described above, additional medical devices or peripheral devices may be connected to patient care device 312 through one or more auxiliary interfaces 362.

Each functional module 316, 318, 320, 322 may include module-specific components 376, a microprocessor 370, a volatile memory 372 and a nonvolatile memory 374 for storing information. It should be noted that while four functional modules are shown in FIG. 7, any number of devices may be connected directly or indirectly to central control unit 314. The number and type of functional modules described herein are intended to be illustrative, and in no way limit the scope of the subject technology. Module-specific components 376 include any components necessary for operation of a particular module, such as a pumping mechanism for infusion pump module 316.

While each functional module may be capable of a least some level of independent operation, interface unit 314 monitors and controls overall operation of device 312. For example, as will be described in more detail below, interface unit 314 provides programming instructions to the functional modules 316, 318, 320, 322 and monitors the status of each module.

Patient care device 312 is capable of operating in several different modes, or personalities, with each personality defined by a configuration database. The configuration database may be a database on storage unit 356 internal to patient care device 312, or an external database 337. A particular configuration database is selected based, at least in part, by patient-specific information such as device or patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 260 location in the hospital or hospital computer network. Patient care information may be entered through network connection 352 or any of input/interface devices 354, 360 or 362, and may originate from anywhere in network 310, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 312 and network 310 may communicate via automated interaction, manual interaction or a combination of both automated and manual interaction. Automated interaction may be continuous or intermittent and may occur through direct network connection 354 (as shown in FIG. 7), or through RS232 links, MIB systems, RF links such as BLUETOOTH, IR links, WLANS, digital cable systems, telephone modems or other wired or wireless communication means. Manual interaction between patient care device 312 and network 310 involves physically transferring, intermittently or periodically, data between systems using, for example, user interface device 354, coded data input device 360, bar codes, computer disks, portable data assistants, memory cards, or any other media for storing data. The communication means in various aspects is bidirectional with access to data from as many points of the distributed data sources as possible. Decision-making can occur at a variety of places within network 310. For example, and not by way of limitation, decisions can be made in HIS server 330, decision support 348, remote data server 349, hospital department or unit stations 346, or within patient care device 312 itself.

All direct communications with medical devices operating on a network in accordance with the subject technology may be performed through information system server 330, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

A medical device including one or more of the features described may be implemented as an ambulatory medical device. Ambulatory medical devices generally refer to devices designed to be portable to support administration of medication during transportation of a patient or remote medication administration (e.g., outside of a health care facility such as in a user's home). U.S. Pat. No. 7,163,381 to Barak describes a pump that may be suitable for ambulatory care and modified to assist in providing safe administration during mobility events. The disclosure of U.S. Pat. No. 7,163,381 is incorporated by reference in its entirety.

Figure 8:
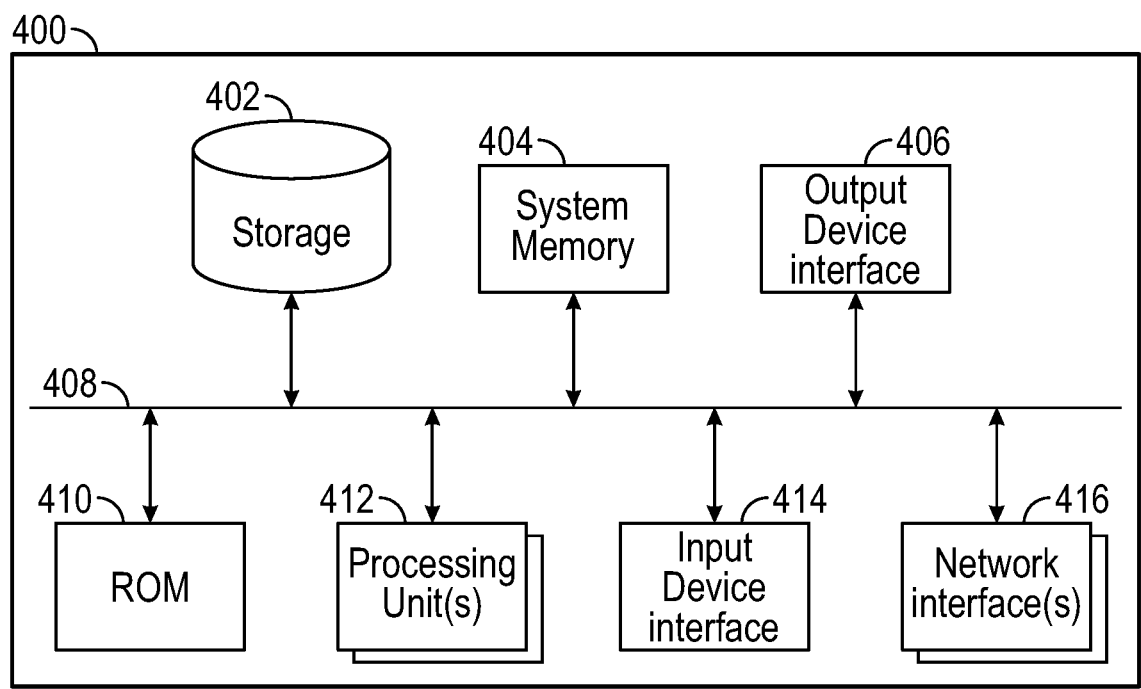
FIG. 8 is a conceptual diagram illustrating an example electronic system for communication with and control of a modular power and connectivity assembly, according to aspects of the subject technology.

FIG. 8 is a conceptual diagram illustrating an example electronic system 400 for powering, communicating, monitoring and controlling of a medical device (e.g., infusion device 110), according to aspects of the subject technology. Electronic system 400 may be a computing device for execution of software associated with one or more components and processes provided by FIGS. 1-7, including but not limited to information system server 330, device terminal 332, computing hardware within patient care device 312, or external database 337. Electronic system 400 may be representative, in combination with the disclosure regarding FIGS. 1-7. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 414, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interfaces 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 8, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

Figure 9:
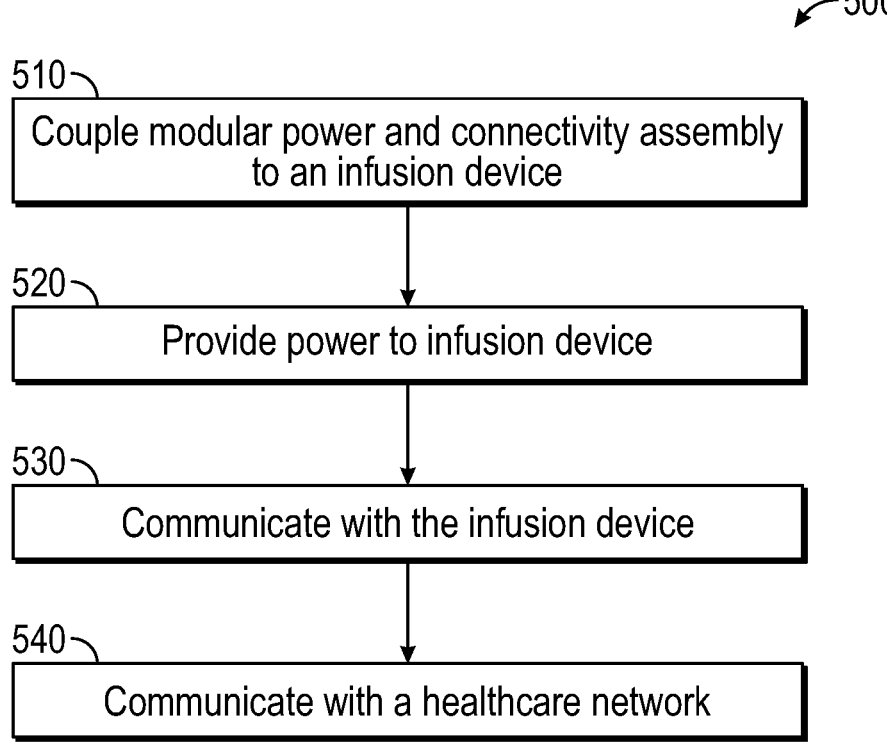
FIG. 9 depicts a method of operating a modular power and connectivity system.

With reference to FIG. 9, a method 500 of operating a modular power and connectivity assembly 100 is provided. In step 510, a modular power and connectivity assembly 100 is coupled to an infusion device 110. For example, an infusion device 110 connected to a tube 24 may be inserted into housing 105 or connected to a base 122 of a harness assembly 120.

The modular power and connectivity assembly 100 provides power to the infusion device 110 in step 520. For example, the modular power and connectivity assembly 100 may transmit power to through a physical connection (e.g., pin, cable) between the housing 105 and the infusion device 110, or through a wireless power transmission between the modular power and connectivity assembly 100 and the infusion device 110.

In step 530, the modular power and connectivity assembly 100 communicates with the infusion device 110. For example, the modular power and connectivity assembly 100 may receive sensor information from the infusion device 110 and/or transmit control information to the infusion device 110.

In step 540, the modular power and connectivity assembly 100 communicates with a healthcare network. For example, the modular power and connectivity assembly 100 may transmit received data or sensor information to a connectivity hub 200, which in turn may be transmitted to a cloud interface 250 and end up being received by a user interface 260. Thus, the user interface 260, such as a mobile interface 270, may provide data or information from the infusion device 110 to a user (e.g., healthcare worker). As another example, the modular power and connectivity assembly 100 may receive control information from the connectivity hub 200, which in turn may be received from the cloud interface 250, which in turn is received from the user interface 260. Thus, the user interface 260, such as a mobile interface 270, may provide control information from the healthcare worker to the infusion device 110.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

The functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

The term web site, as used herein, may include any aspect of a web site, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A modular power and connectivity assembly, comprising:
   a device coupling member comprising a sensor for sensing pressure of a fluid flowing through an infusion tube;
   a housing comprising: a cavity comprising a cavity coupling member; a power assembly configured to provide power to the sensor; and a communication assembly configured to provide communication with the sensor;
   and a harness assembly including an external base disposed outside of the housing and an extension member, wherein the sensor is coupled to the external base and the extension member couples the external base to the housing within the cavity, wherein the modular power and connectivity assembly is configured to be reusable, wherein the modular power and connectivity assembly is configured to be removably coupled to the sensor, and wherein the device coupling member and the cavity coupling member are wireless assemblies configured to wirelessly communicate with each other.

2. The modular power and connectivity assembly of claim 1, further comprising a recess configured to receive a portion of the infusion tube.

3. The modular power and connectivity assembly of claim 1, further comprising at least one indicator configured to visually indicate a level of power stored in the power assembly.

4. The modular power and connectivity assembly of claim 1, wherein the cavity is sized and dimensioned to receive the sensor.

5. The modular power and connectivity assembly of claim 1, wherein the device coupling member and the cavity coupling member are opposing connections configured to physically mate with each other.

6. The modular power and connectivity assembly of claim 1, wherein the device coupling member and the cavity coupling member are magnet assemblies configured to magnetically attract each other.

7. The modular power and connectivity assembly of claim 1, wherein the harness assembly comprises the device coupling member and the external base, and wherein the cavity comprises the cavity coupling member configured to physically mate with the device coupling member.

8. The modular power and connectivity assembly of claim 1, wherein the external base is configured to physically mate with the sensor.

9. The modular power and connectivity assembly of claim 1, wherein the external base is configured to magnetically mate with the sensor.

10. The modular power and connectivity assembly of claim 1, wherein the external base is configured to wirelessly connect with the sensor.

11. The modular power and connectivity assembly of claim 1, wherein the power assembly comprises one or more rechargeable batteries.

12. A power and connectivity system, comprising: one or more reusable modular power and connectivity assemblies, each modular power and connectivity assembly comprising:
a device coupling member comprising a sensor for sensing pressure of a fluid flowing through an infusion tube;
a housing having a cavity comprising a cavity coupling member, the housing comprising: a power assembly configured to provide power to the sensor; and a communication assembly configured to provide communication with the sensor, wherein each modular power and connectivity assembly is configured to be removably coupled to the sensor;
and a harness assembly including an external base disposed outside of the housing and an extension member, wherein the sensor is coupled to the external base and the extension member couples the external base to the housing within the cavity, wherein the device coupling member and the cavity coupling member are wireless assemblies configured to wirelessly communicate with each other; and a connectivity hub configured to transmit electronic signals to and receive electronic signals from the one or more reusable modular power and connectivity assemblies.

13. The power and connectivity system of claim 12, further comprising a cloud interface configured to transmit electronic signals to and receive electronic signals from the connectivity hub.

14. The power and connectivity system of claim 13, further comprising a mobile interface configured to transmit electronic signals to and receive electronic signals from the cloud interface, wherein the mobile interface resides on a portable electronic device.

15. The power and connectivity system of claim 12, further comprising a charging station configured to recharge the one or more reusable modular power and connectivity assemblies.

16. The power and connectivity system of claim 15, wherein the charging station comprises a rechargeable power source, and wherein the charging station is configured to be portable.

17. A method of operating the power and connectivity system of claim 12, the method comprising: removably coupling the modular power and connectivity assembly to the sensor; transmitting power from the modular power and connectivity assembly to the sensor; providing a communication link between the modular power and connectivity assembly and the sensor; transmitting data from the sensor to the modular power and connectivity assembly; transmitting at least a portion of the data from the modular power and connectivity assembly to the connectivity hub; and transmitting the portion of the data from the connectivity hub to a cloud interface of a healthcare network.

* * * * *